(12) United States Patent
Saiga et al.

(10) Patent No.: US 9,955,693 B2
(45) Date of Patent: May 1, 2018

(54) METHOD FOR CONTROLLING PHYTOPATHOGENIC FILAMENTOUS FUNGI OTHER THAN OOMYCETE MICROORGANISMS

(71) Applicant: Nippon Soda Co., Ltd., Chiyoda-ku, Tokyo (JP)

(72) Inventors: Tomoyuki Saiga, Makinohara (JP); Kazushige Kato, Makinohara (JP); Shinya Watanabe, Makinohara (JP); Akie Fukuyo, Makinohara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days. days.

(21) Appl. No.: 14/771,262

(22) PCT Filed: Feb. 24, 2014

(86) PCT No.: PCT/JP2014/054355
§ 371 (c)(1),
(2) Date: Aug. 28, 2015

(87) PCT Pub. No.: WO2014/136603
PCT Pub. Date: Sep. 12, 2014

(65) Prior Publication Data
US 2016/0000083 A1    Jan. 7, 2016

(30) Foreign Application Priority Data

Mar. 5, 2013 (JP) ................. 2013-042625

(51) Int. Cl.
*A01N 47/18* (2006.01)
*A01N 47/40* (2006.01)
*A01N 43/713* (2006.01)

(52) U.S. Cl.
CPC ........... *A01N 47/18* (2013.01); *A01N 43/713* (2013.01)

(58) Field of Classification Search
None
See application file for complete search history.

(56) References Cited

U.S. PATENT DOCUMENTS

| | | | |
|---|---|---|---|
| 2005/0070439 A1 | 3/2005 | Kobori et al. | |
| 2007/0105926 A1* | 5/2007 | Kobori | C07D 401/12 514/381 |
| 2011/0015236 A1* | 1/2011 | Beier | A01N 43/713 514/340 |
| 2011/0201613 A1 | 8/2011 | Beier et al. | |
| 2013/0005672 A1 | 1/2013 | Urihara | |
| 2013/0012546 A1 | 1/2013 | Beier et al. | |
| 2014/0005229 A1 | 1/2014 | Nakamura et al. | |

FOREIGN PATENT DOCUMENTS

| | | | |
|---|---|---|---|
| CN | 102725282 A | 10/2012 | |
| JP | 2009-269913 A | 11/2009 | |
| JP | 2010-248273 A | 11/2010 | |
| JP | 2011-515368 A | 5/2011 | |
| JP | 2011-520778 A | 7/2011 | |
| WO | WO 03/016303 A1 | 2/2003 | |
| WO | WO 2009/115556 A1 | 9/2009 | |
| WO | WO 2009/115557 A2 | 9/2009 | |
| WO | WO 2011029551 A2 * | 3/2011 | ............ A01N 43/90 |
| WO | WO 2012/045798 A1 | 4/2012 | |
| WO | WO 2012/128135 A1 | 9/2012 | |
| WO | WO 2012143127 A1 * | 10/2012 | ............ A01N 43/56 |
| WO | WO 2013/024008 A1 | 2/2013 | |

OTHER PUBLICATIONS

International Search Report dated Mar. 18, 2014, in PCT/JP2014/054355.
Supplementary European Search Report dated Jun. 20, 2016, in EP 14760550.5.
Office Action dated Mar. 23, 2016, in CN 201480011557.3, with English translation.
Office Action dated Jul. 6, 2017, in EP 14760550.5.

* cited by examiner

*Primary Examiner* — Kamal Saeed
(74) *Attorney, Agent, or Firm* — Foley & Lardner LLP

(57) ABSTRACT

Phytopathogenic filamentous fungi other than oomycete microorganisms are controlled using at least one compound selected from among tetrazoyloxime derivatives represented by formula (I) and salts thereof.

[Chemical Formula 1]

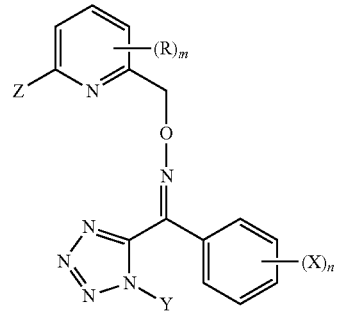

In formula (I), X represents a C1 to C6 alkyl group or the like, n represents an integer of 0 to 5, Y represents a C1 to C6 alkyl group, Z represents a hydrogen atom or an amino group or the like, Q represents a hydrogen atom or a C1 to C8 alkyl group or the like, R represents a halogeno group or a C1 to C6 alkoxy group, and m represents an integer of 0 to 3.

3 Claims, No Drawings

METHOD FOR CONTROLLING PHYTOPATHOGENIC FILAMENTOUS FUNGI OTHER THAN OOMYCETE MICROORGANISMS

TECHNICAL FIELD

The present invention relates to a method for controlling phytopathogenic filamentous fungi other than oomycete microorganisms. More specifically, the present invention relates to a method for controlling phytopathogenic filamentous fungi other than oomycete microorganisms with superior efficacy using a low concentration of an active ingredient.

Priority is claimed on Japanese Patent Application No. 2013-042625, filed Mar. 5, 2013, the content of which is incorporated herein by reference.

BACKGROUND ART

Patent Document 1 discloses that a tetrazoyloxime derivative and agricultural chemicals containing the tetrazoyloxime derivative as an active ingredient exhibit a particularly powerful effect in the prevention and treatment of plant diseases caused by fungi of the genus *Pythium* including *Pythium ultimum*, the genus *Aphanomyces*, or oomycetes belonging to closely related genera.

Further, Patent Document 2 discloses that a tetrazoyloxime derivative and agricultural chemicals containing the tetrazoyloxime derivative as an active ingredient exhibit effectiveness against plant diseases caused by various filamentous fungi including oomycetes, zygomycetes, ascomycetes, basidiomycetes and deuteromycetes. The publication specifically mentions powerful effects upon the oomycetes Plasmopara viticola and Phytophthora infestans.

PRIOR ART LITERATURE

Patent Documents

Patent Document 1: JP 2009-269913 A
Patent Document 2: WO 03/016303

DISCLOSURE OF INVENTION

Problems to be Solved by the Invention

Incidentally, symptoms similar to the damage caused to rice plants by damping-off fungi can also be caused by phytopathogenic filamentous fungi belonging to the genus *Rhizopus* or the genus *Fusarium*. However, minimal investigation has been conducted relating to effective methods for controlling these types of phytopathogenic filamentous fungi other than oomycete microorganisms.

A problem of the present invention is to provide a method for controlling phytopathogenic filamentous fungi other than oomycete microorganisms with superior efficacy using a low concentration of an active ingredient.

Means for Solving the Problems

As a result of investigations aimed at solving the above problem, the inventors of the present invention discovered that a tetrazoyloxime derivative of a specific structure exhibited a superior control effect against phytopathogenic filamentous fungi other than oomycete microorganisms. The present invention was completed on the basis of this finding.

In other words, the present invention includes the aspects described below.

[1] A method for controlling phytopathogenic filamentous fungi other than oomycete microorganisms using at least one compound selected from among tetrazoyloxime derivatives represented by formula (I) and salts thereof

[Chemical Formula 1]

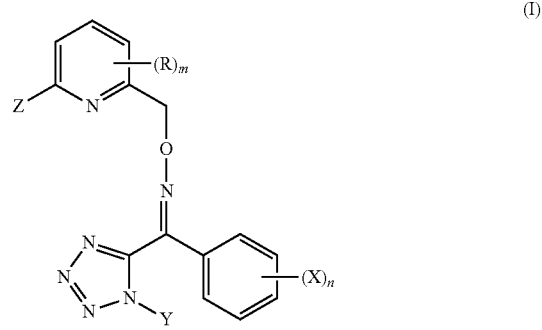

(I)

In formula (I), X represents a C1 to C6 alkyl group, a C1 to C6 alkoxy group, a halogeno group, a nitro group, a cyano group, a C6 to C10 aryl group or a C1 to C6 alkylsulfonyl group. Further, n represents an integer of 0 to 5, and when n is 2 or greater, the X groups may be the same or different.

Y represents a C1 to C6 alkyl group.

Z represents a hydrogen atom, an amino group, or a group represented by NHC(=O)—Q.

Q represents a hydrogen atom, a C1 to C8 alkyl group, a halo C1 to C6 alkyl group, a C3 to C6 cycloalkyl group, a C3 to C6 cycloalkyl C1 to C4 alkyl group, a C1 to C8 alkoxy group, a C3 to C6 cycloalkyloxy group, a C3 to C6 cycloalkyloxy C1 to C4 alkyl group, a C3 to C6 cycloalkyl C1 to C4 alkoxy group, a C3 to C6 cycloalkyloxy C1 to C4 alkoxy group, a C7 to C20 aralkyloxy group that may be substituted with a halogeno group or a C1 to C6 alkoxy group, a C8 to C20 aralkenyloxy group that may be substituted with a halogeno group or a C1 to C6 alkoxy group, a 5- to 10-membered heterocyclyl C1 to C6 alkoxy group that may be substituted with a halogeno group or a C1 to C6 alkoxy group, a 5- to 10-membered heterocyclyl C2 to C6 alkenyloxy group that may be substituted with a halogeno group or a C1 to C6 alkoxy group, a C1 to C4 alkylthio C1 to C8 alkyl group, a C1 to C4 alkoxy C1 to C6 alkyl group, a C1 to C4 acylamino C1 to C6 alkyl group, a C1 to C4 alkoxyimino C1 to C6 alkyl group, a C1 to C4 acylamino C1 to C6 alkoxy group, a C1 to C4 alkoxyimino C1 to C6 alkoxy group, a C1 to C8 alkylamino group, a C2 to C6 alkenyl group, a C7 to C20 aralkyl group that may be substituted with a halogeno group or a C1 to C6 alkoxy group, a C8 to C20 aralkenyl group that may be substituted with a halogeno group or a C1 to C6 alkoxy group, a 5- to 10-membered heterocyclyl C1 to C6 alkyl group that may be substituted with a halogeno group or a C1 to C6 alkoxy group, a 5- to 10-membered heterocyclyl C2 to C6 alkenyl group that may be substituted with a halogeno group or a C1 to C6 alkoxy group, a C6 to C10 aryl group that may be substituted with a halogeno group or a C1 to C6 alkoxy group, or a 5- to 10-membered heterocyclyl group that may be substituted with a halogeno group or a C1 to C6 alkoxy group.

R represents a halogeno group or a C1 to C6 alkoxy group. Further, m represents an integer of 0 to 3, and when m is 2 or greater, the R groups may be the same or different.

[2] The method disclosed in [1], wherein the phytopathogenic filamentous fungi other than oomycete microorganisms belong to the genus *Rhizopus* or the genus *Fusarium*.

Effects of the Invention

The control method according to the present invention can, with a low concentration of the active ingredient, effectively control phytopathogenic filamentous fungi other than oomycete microorganisms, such as fungi of the genus *Rhizopus* and the genus *Fusarium* and the like, which can cause symptoms known as damping-off in a variety of crops.

DESCRIPTION OF THE EMBODIMENTS

Preferred examples of the present invention are described below, but the present invention is in no way limited by these examples. Various additions, omissions, substitutions and other modifications can be made without departing from the spirit or scope of the present invention.

The control method according to the present invention uses at least one compound selected from among specific tetrazoyloxime derivatives and salts thereof.

The tetrazoyloxime derivative used in the present invention is a compound represented by formula (I).

In formula (I), X represents a C1 to C6 alkyl group, a C1 to C6 alkoxy group, a halogeno group, a nitro group, a cyano group, a C6 to C10 aryl group or a C1 to C6 alkylsulfonyl group. Further, n represents an integer of 0 to 5, and when n is 2 or greater, the X groups may be the same or different.

Among these possibilities, X is preferably a C1 to C6 alkyl group, a C1 to C6 alkoxy group, a halogeno group, a nitro group, a cyano group or a C1 to C6 alkylsulfonyl group.

Further, n is preferably 0 or 1, and is more preferably 0.

Examples of the C1 to C6 alkyl group include a methyl group, an ethyl group, a n-propyl group, an i-propyl group, a n-butyl group, a s-butyl group, an i-butyl group, a t-butyl group, a n-pentyl group and a n-hexyl group.

Examples of the C1 to C6 alkoxy group include a methoxy group, an ethoxy group, a n-propoxy group, an i-propoxy group, a n-butoxy group, a s-butoxy group, an i-butoxy group and a t-butoxy group.

Examples of the halogeno group include a fluoro group, a chloro group, a bromo group and an iodo group.

Examples of the C6 to C10 aryl group include a phenyl group and a naphthyl group.

Examples of the C1 to C6 alkylsulfonyl group include a methylsulfonyl group, an ethylsulfonyl group and a t-butylsulfonyl group.

In formula (I), Y represents a C1 to C6 alkyl group. Examples of the C1 to C6 alkyl group for Y include the same groups as those already mentioned.

In formula (I), Z represents a hydrogen atom, an amino group, or a group represented by NHC(=O)—Q. Among these possibilities, Z is preferably a group represented by NHC(=O)—Q.

Q represents a hydrogen atom, a C1 to C8 alkyl group, a halo C1 to C6 alkyl group, a C3 to C6 cycloalkyl group, a C3 to C6 cycloalkyl C1 to C4 alkyl group, a C1 to C8 alkoxy group, a C3 to C6 cycloalkyloxy group, a C3 to C6 cycloalkyloxy C1 to C4 alkyl group, a C3 to C6 cycloalkyl C1 to C4 alkoxy group, a C3 to C6 cycloalkyloxy C1 to C4 alkoxy group, a C7 to C20 aralkyloxy group that may be substituted with a halogeno group or a C1 to C6 alkoxy group, a C8 to C20 aralkenyloxy group that may be substituted with a halogeno group or a C1 to C6 alkoxy group, a 5- to 10-membered heterocyclyl C1 to C6 alkoxy group that may be substituted with a halogeno group or a C1 to C6 alkoxy group, a 5- to 10-membered heterocyclyl C2 to C6 alkenyloxy group that may be substituted with a halogeno group or a C1 to C6 alkoxy group, a C1 to C4 alkylthio C1 to C8 alkyl group, a C1 to C4 alkoxy C1 to C6 alkyl group, a C1 to C4 acylamino C1 to C6 alkyl group, a C1 to C4 alkoxyimino C1 to C6 alkyl group, a C1 to C4 acylamino C1 to C6 alkoxy group, a C1 to C4 alkoxyimino C1 to C6 alkoxy group, a C1 to C8 alkylamino group, a C2 to C6 alkenyl group, a C7 to C20 aralkyl group that may be substituted with a halogeno group or a C1 to C6 alkoxy group, a C8 to C20 aralkenyl group that may be substituted with a halogeno group or a C1 to C6 alkoxy group, a 5- to 10-membered heterocyclyl C1 to C6 alkyl group that may be substituted with a halogeno group or a C1 to C6 alkoxy group, a 5- to 10-membered heterocyclyl C2 to C6 alkenyl group that may be substituted with a halogeno group or a C1 to C6 alkoxy group, a C6 to C10 aryl group that may be substituted with a halogeno group or a C1 to C6 alkoxy group, or a 5- to 10-membered heterocyclyl group that may be substituted with a halogeno group or a C1 to C6 alkoxy group.

Among these possibilities, Q is preferably a C1 to C8 alkoxy group or a C3 to C6 cycloalkyloxy group.

Moreover, Q is more preferably a C1 to C8 alkoxy group.

Examples of the C6 to C10 aryl group for Q include the same groups as those already mentioned.

A heterocyclyl group means an aromatic hetero ring, a saturated hetero ring, an unsaturated hetero ring, or a condensed heterocycle in which a hetero ring and a benzene ring are condensed, wherein the hetero ring contains from one to four non-carbon hetero atoms selected from among a nitrogen atom, an oxygen atom and a sulfur atom as the atoms that constitute the hetero ring. Examples of the 5- to 10-membered heterocyclyl group include a furan-2-yl group, a furan-3-yl group, a thiophen-2-yl group, a thiophen-3-yl group, a pyrrol-1-yl group, a pyrrol-2-yl group, a pyrrol-3-yl group, a pyridin-2-yl group, a pyridin-3-yl group, a pyridin-4-yl group, a pyrazin-2-yl group, a pyrazin-3-yl group, a pyrimidin-2-yl group, a pyrimidin-4-yl group, a pyrimidin-5-yl group, a pyridazin-3-yl group, a pyridazin-4-yl group, a pyrrolidin-2-yl group, a pyrrolidin-3-yl group, a piperidin-2-yl group, a piperidin-4-yl group, a tetrahydrofuran-2-yl group, a tetrahydrofuran-3-yl group, a morpholin-2-yl group, a morpholin-3-yl group, a morpholin-4-yl group, a 1,3-dioxan-2-yl group, a 1,3-dioxan-4-yl group, a 1,3-dioxan-5-yl group, a 1,4-dioxan-2-yl group, a 1,4-dioxin-2-yl group, a imidazol-1-yl group, a imidazol-2-yl group, an imidazol-4-yl group, a pyrazol-1-yl group, a pyrazol-3-yl group, a pyrazol-4-yl group, a pyrazol-5-yl group, a thiazol-2-yl group, a thiazol-4-yl group, a thiazol-5-yl group, an oxazol-2-yl group, an oxazol-4-yl group, an oxazol-5-yl group, an isoxazol-3-yl group, an isoxazol-4-yl group, an isoxazol-5-yl group, a 1,3,4-thiadiazol-2-yl group, a 1,2,3-triazol-1-yl group, a 1,2,4-triazol-1-yl group, a tetrazol-1-yl group, a tetrazol-2-yl group, a 1,3-benzodioxol-4-yl group, a 1,4-benzodioxan-5-yl group, a 1,4-benzodioxan-6-yl group, a 2,3-dihydrobenzofuran-4-yl group, a 2,3-dihydrobenzofuran-5-yl group, a benzofuran-2-yl group, a benzofuran-3-yl group, a benzothiophen-2-yl group, a benzothiophen-3-yl group, a quinoxalin-2-yl group, a quinoxalin-5-yl group, an indol-1-yl group, an indol-2-yl group, an indol-3-yl group, a benzimidazol-1-yl group, a benzimidazol-2-yl group, a benzothiazol-2-yl group, a benzothiazol-4-yl group, a benzoxazol-2-yl group, a benzoxazol-4-yl group, a quinolin-2-yl group, a quinolin-3-yl group, an isoquinolin-1-yl group, and an isoquinolin-3-yl group.

Examples of the C1 to C8 alkyl group include a methyl group, an ethyl group, a n-propyl group, an i-propyl group, a n-butyl group, a s-butyl group, an i-butyl group, a t-butyl group, a n-pentyl group, a n-hexyl group and a n-octyl group.

Examples of the halo C1 to C6 alkyl group include a chloromethyl group, a chloroethyl group, a trifluoromethyl group, a 1,2-dichloro-n-propyl group, a 1-fluoro-n-butyl group and a perfluoro-n-pentyl group.

Examples of the C3 to C6 cycloalkyl group include a cyclopropyl group, a cyclobutyl group, a cyclopentyl group and a cyclohexyl group.

Examples of the C3 to C6 cycloalkyl C1 to C4 alkyl group include a cyclopropylmethyl group, a 1-cyclopropylethyl group, a 2-cyclopropylethyl group and a cyclobutylmethyl group.

Examples of the C1 to C8 alkoxy group include a methoxy group, an ethoxy group, a n-propoxy group, an i-propoxy group, a n-butoxy group, a s-butoxy group, an i-butoxy group, a t-butoxy group and a n-octoxy group.

Examples of the C3 to C6 cycloalkyloxy group include a cyclopropyloxy group, a cyclobutyloxy group, a cyclopentyloxy group and a cyclohexyloxy group.

Examples of the C3 to C6 cycloalkyloxy C1 to C4 alkyl group include a cyclopropyloxymethyl group, a 1-cyclopropyloxyethyl group, a 2-cyclopropyloxyethyl group and a cyclobutyloxymethyl group.

Examples of the C3 to C6 cycloalkyl C1 to C4 alkoxy group include a cyclopropylmethoxy group, a 1-cyclopropylethoxy group, a 2-cyclopropylethoxy group and a cyclobutylmethoxy group.

Examples of the C3 to C6 cycloalkyloxy C1 to C4 alkoxy group include a cyclopropyloxymethoxy group, a 1-cyclopropyloxyethoxy group, a 2-cyclopropyloxyethoxy group and a cyclobutyloxymethoxy group.

Examples of the C7 to C20 aralkyloxy group include a benzyloxy group and a phenethyloxy group.

Examples of the C8 to C20 aralkenyloxy group include a 2-phenylethenyloxy group and a 2-naphthylethenyloxy group.

Examples of the 5- to 10-membered heterocyclyl C1 to C6 alkoxy group include a pyridin-2-yl-methoxy group, a pyridin-2-yl-2-ethoxy group, a pyridin-3-yl-methoxy group, a pyridin-4-yl-1-ethoxy group, a furan-3-yl-1-ethoxy group, a thiophen-2-yl-methoxy group and a pyrrol-2-yl-2-ethoxy group.

Examples of the 5- to 10-membered heterocyclyl C2 to C6 alkenyloxy group include a pyridin-2-yl-2-ethenyloxy group and a pyridin-3-yl-2-ethenyloxy group.

Examples of the C1 to C4 alkylthio C1 to C8 alkyl group include a methylthioethyl group, an ethylthiomethyl group, a n-propylthiomethyl group, an i-propylthiomethyl group, a n-butylthiomethyl group, an i-butylthiomethyl group, a s-butylthiomethyl group and a t-butylthiomethyl group.

Examples of the C1 to C4 alkoxy C1 to C6 alkyl group include a methoxybutyl group, an ethoxypropyl group, a n-propoxyethyl group, an i-propoxyethyl group, a n-butoxymethyl group, a s-butoxymethyl group, an i-butoxymethyl group and a t-butoxymethyl group.

Examples of the C1 to C4 acylamino C1 to C6 alkyl group include a formylaminobutyl group, an acetylaminopropyl group, a propanoylaminoethyl group, butyrylaminomethyl group, an i-propylcarbonylaminomethyl group and a benzoylaminomethyl group.

Examples of the C1 to C4 alkoxyimino C1 to C6 alkyl group include a methoxyiminomethyl group, a 1-methoxyiminoethyl group, a 2-methoxyiminoethyl group, an ethoxyiminomethyl group and a 1-ethoxyiminomethyl group.

Examples of the C1 to C4 acylamino C1 to C6 alkoxy group include a formylaminobutoxy group, an acetylaminopropoxy group, a propanoylaminoethoxy group, a butyrylaminomethoxy group, an i-propylcarbonylaminomethoxy group and a benzoylaminomethoxy group.

Examples of the C1 to C4 alkoxyimino C1 to C6 alkoxy group include a methoxyiminomethoxy group, a 1-methoxyiminoethoxy group, a 2-methoxyiminoethoxy group, an ethoxyiminomethoxy group and a 1-ethoxyiminomethoxy group.

Examples of the C1 to C8 alkylamino group include a methylamino group, a dimethylamino group and a diethylamino group.

Examples of the C2 to C6 alkenyl group include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group and a 5-hexenyl group.

Examples of the C7 to C20 aralkyl group include a benzyl group and a phenethyl group.

Examples of the C8 to C20 aralkenyl group include a 1-phenylethenyl group and a 2-phenylethenyl group.

Examples of the 5- to 10-membered heterocyclyl C1 to C6 alkyl group include a pyridin-2-yl-methyl group, a pyridin-3-yl-1-ethyl group and a pyridin-4-yl-2-ethyl group.

Examples of the 5- to 10-membered heterocyclyl C2 to C6 alkenyl group include a pyridin-2-yl-1-ethenyl group, a pyridin-3-yl-2-ethenyl group and a pyridin-4-yl-2-ethenyl group.

In formula (I), R represents a halogeno group or a C1 to C6 alkoxy group. Further, m represents an integer of 0 to 3, and when m is 2 or greater, the R groups may be the same or different. Examples of the halogeno group and C1 to C6 alkoxy group for R include the same groups as those already mentioned.

Further, m is preferably 0 or 1, and is more preferably 0.

The salt used in the present invention is a salt of the compound represented by formula (I). There are no particular limitations on this salt, provided it is permissible for use in agriculture and horticulture. Specific examples of the salt include salts of inorganic acids such as a hydrochloride, a nitrate, a sulfate or a phosphate, and salts of organic acids such as an acetate, a lactate, a propionate or a benzoate.

Specific examples of the tetrazoyloxime derivative represented by formula (I) that is used in the present invention include compounds disclosed in Patent Document 2.

Among the tetrazoyloxime derivatives represented by formula (I) that can be used in the present invention, an example of a particularly preferred compound is the compound represented by formula (II) (hereafter referred to as "compound II").

[Chemical Formula 2]

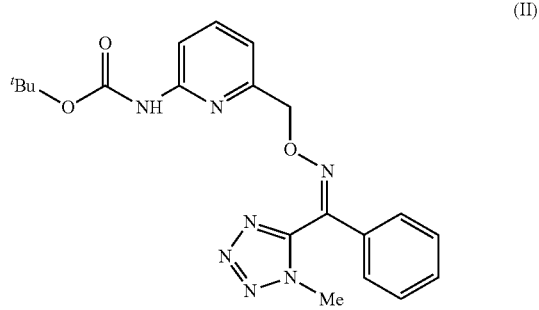

(II)

The nitrogen-containing heterocyclic compounds represented by formula (I) and the salts thereof can be produced using known methods such as the methods disclosed in Patent Document 1 and Patent Document 2.

There are no particular limitations on the way in which the nitrogen-containing heterocyclic compound represented by formula (I) or the salt thereof is used in the control method according to the present invention, and the types of methods used for conventional control agents can be employed.

In the control method according to the present invention, the nitrogen-containing heterocyclic compound represented by formula (I) or the salt thereof can be used either as is, or within a formulation. There are no particular limitations on the form of this formulation, and any of the forms that can be adopted in typical agricultural and horticultural chemicals can be adopted, including dustable powders, wettable powders, water soluble powders, emulsifiable concentrates, flowable agents, pellets and granules and the like.

There are no particular limitations on the types of auxiliary materials that can be used in preparing the above formulations. Examples of these auxiliary materials include solid carriers, solvents, surfactants, and other additives.

Specific examples of the solid carriers include plant-based powders such as soy flour or wheat flour, and mineral-based fine powders such as silica dioxide, diatomaceous earth, apatite, gypsum, talc, bentonite, pyrophyllite, clay and joint soil.

Specific examples of the solvents include kerosene, xylene, petroleum distillates such as solvent naphtha, cyclohexane, cyclohexanone, dimethylformamide, dimethyl sulfoxide, alcohol, acetone, methyl isobutyl ketone, mineral oils, plant oils and water.

Specific examples of the surfactants include nonionic surfactants such as polyoxyethylene adducts of alkyl phenyl ethers, polyoxyethylene adducts of alkyl ethers, polyoxyethylene adducts of higher fatty acid esters, polyoxyethylene adducts of sorbitan higher fatty acid esters and polyoxyethylene adducts of tristyryl phenyl ether, as well as sulfate ester salts of polyoxyethylene adducts of alkyl phenyl ethers, alkylbenzene sulfonates, sulfate ester salts of higher alcohols, alkylnaphthalene sulfonates, polycarboxylates, lignin sulfonates, formaldehyde condensation products of alkylnaphthalene sulfonates, and isobutylene-maleic anhydride copolymers.

Specific examples of the additives include organic and inorganic compounds such as sodium benzoate, urea and salt cake, oils such as rapeseed oil, soybean oil, sunflower oil, castor oil, pine oil and cottonseed oil, and derivatives and concentrates of these oils.

The amount of the nitrogen-containing heterocyclic compound represented by formula (I) or the salt thereof incorporated within the formulation may be set appropriately in accordance with the particular formulation used, but is preferably within a range from 0.5 to 95% by mass, and more preferably from 2 to 70% by mass. For example, in the case of a water-dispersible powder, the amount is preferably from 5 to 90% by weight, and more preferably from 10 to 85% by weight, in the case of an emulsion, the amount is preferably from 3 to 70% by weight, and more preferably from 5 to 60% by weight, and in the case of granules, the amount is preferably from 0.01 to 50% by weight, and more preferably from 0.05 to 40% by weight.

Further, conventional germicides, insecticides, miticides, and synergists and the like may be mixed with the nitrogen-containing heterocyclic compound represented by formula (I) or the salt thereof, or with the formulation thereof.

In the control method according to the present invention, the nitrogen-containing heterocyclic compound represented by formula (I) or the salt thereof can be used within a variety of application methods, including foliage application, soil application, water surface application and seed treatment. The amount applied varies depending on the plant being treated and the plant disease being targeted, but in the case of foliage application, a solution having an active ingredient concentration within a range from 1 to 10,000 ppm, and preferably 10 to 1,000 ppm is preferably applied at a rate of 50 to 300 L per 10 are, in the case of soil application or water surface application, the application of 0.1 to 1,000 g, and particularly 10 to 100 g, of the active ingredient per 10 are is preferable, and in the case of a seed treatment, the application of 0.001 to 50 g of the active ingredient per 1 kg of seeds is preferable.

Examples of the phytopathogenic filamentous fungi other than oomycete microorganisms targeted by the control method according to the present invention include zygomycetes, ascomycetes, basidiomycetes and deuteromycetes.

Among these, the control method according to the present invention can be used favorably against fungi of the genus *Rhizopus* and the genus *Mucor* belonging to the zygomycetes, and fungi of the genus *Fusarium*, the genus *Trichoderma* and the genus *Phoma* belonging to the deuteromycetes (or ascomycetes).

Moreover, among these, the control method according to the present invention can be used particularly effectively against fungi of the genus *Rhizopus* and the genus *Fusarium*.

There are no particular limitations on the fungi belonging to the genus *Rhizopus*, and examples include phytopathogens that cause rice seedling damping-off (*Rhizopus* oryzae, *Rhizopus* chinensis, *Rhizopus* javanicus, *Rhizopus* arrhizus), satsumaimo fuhai-byo (*Rhizopus* nodosus, *Rhizopus* oryzae), togarashi hetagusare-byo (*Rhizopus* stolonifer), melon black mold (*Rhizopus* stolonifer), strawberry soft rot (*Rhizopus* nigricans) and lily bulb rot (*Rhizopus* oryzae).

The are no particular limitations on the fungi belonging to the genus *Mucor*, and examples include a phytopathogen that causes rice seedling damping-off (*Mucor fragilis*).

The are no particular limitations on the fungi belonging to the genus *Fusarium*, and examples include phytopathogens that cause rice seedling damping-off (*Fusarium avenaceum, Fusarium solani, Fusarium roseum*), rice scab (*Gibberella zeae* or *Fusarium graminearum*), rice bakanae disease (*Gibberella fujikuroi* or *Fusarium moniliforme*), wheat scab (*Fusarium graminearum, Fusarium culmorum, Fusarium avenaceum, Microdochium nivale*), soybean damping-off (*Gibberella fujikuroi, Fusarium oxysporum*), potato dry rot (*Fusarium solani*), onion *Fusarium* basal rot (*Fusarium* oxysporum), carrot dry rot (*Fusarium solani, Fusarium avenaceum*), and cucumber *Fusarium* wilt (*Fusarium oxysporum*).

There are no particular limitations on the fungi belonging to the genus *Trichoderma*, and examples include a phytopathogen that causes rice seedling damping-off (*Trichoderma viride*).

There are no particular limitations on the fungi belonging to the genus *Phoma*, and examples include phytopathogens that cause rice seedling damping-off (*Phoma* sp.) and asparagus stem blight (*Phoma asparagi*).

These phytopathogenic filamentous fungi other than oomycete microorganisms adhere to and grow on grains, vegetables, root vegetables, tubers, trees, pasture grasses, and lawn grasses and the like. The control method according to the present invention can be performed by targeting any of the various regions of these plant types. Further, among these plant types, the control method according to the present invention can be applied favorably to grains, and among grains, can be applied particularly favorably to rice. Examples of the various regions of plants that may be targeted include the leaves, stems, stalks, flowers, buds, fruit, seeds, sprouts, roots, tubers, tuberous roots, shoots and cuttings. Further, the control method according to the present invention can also be applied to improved or altered varieties, cultivars, mutants, hybrids and genetically modified organisms (GMO) of these plant types.

EXAMPLES

The control method according to the present invention is described below in further detail using a series of examples. However, the present invention is in no way limited by these examples.

Formulation Example 1

Ten parts by mass of the compound II, 2 parts by mass of polyoxyethylene aryl phenyl ether, 0.5 parts by mass of sodium dialkylsulfosuccinate, 5 parts by mass of glycerol, 0.3 parts by mass of xanthan gum, and 82.2 parts by mass of water were mixed together. The resulting mixture was subjected to wet grinding until the particle size was not more than 3 μm, thus obtaining a flowable agent containing 10% of the active ingredient.

<<Control of Rice Seedling Damping-Off (*Fusarium* genus Fungus)>>

Example 1

A fungus culture of *Fusarium roseum* cultivated in a soil bran medium was mixed with a test soil to prepare a contaminated soil.

Small seedling boxes (8.5 cm×8.5 cm×3 cm) filled with this contaminated soil as the bed soil were irrigated by diluting the flowable agent obtained in Formulation Example 1 with water, and applying about 40 ml of the diluted agent uniformly to each seedling box. The active ingredient treatment amount was 2 mg/box.

Rice seeds (of the koshihikari variety) in the so-called hatomune state (in which a bud with a length of about 1 mm was protruding from each rice seed), prepared by subjecting the rice seeds to presoaking and forced germination treatments, were sowed across the entire surface of each seedling box, and an additional amount of the contaminated soil was then used to cover the seeds. The seedling boxes were then placed in a nursery cabinet at 30° C. for 3 days to allow the seeds to germinate. Subsequently, a low-temperature treatment at 4° C. was performed for 3 days. Following this low-temperature treatment, the seedlings were raised inside a glass greenhouse. Twenty eight days after sowing, the number of healthy seedlings (A), the number of withered seedlings (B), the number of stunted seedlings (having a height less than ½ of that of the healthy seedlings) (C), the number of above ground diseased seedlings (D) and the number of root diseased seedlings (E) within each seedling box were counted, and when the disease severity was calculated using the following formula, the result was 15.1.

$$\text{Disease severity} = (B \times 4 + C \times 3 + D \times 2 + E \times 1)/(\text{number of seedlings} \times 4) \times 100$$

$$\text{Number of seedlings} = A + B + C + D + E$$

Comparative Example 1

A hydroxyisoxazole-metalaxyl liquid reagent was diluted with water to obtain a chemical solution containing 0.03% of hydroxyisoxazole and 0.004% of metalaxyl.

With the exception of using this chemical solution instead of the aforementioned water-diluted flowable agent, the disease severity was calculated using the same method as that described for Example 1. Although the active ingredient treatment amount was 13.6 mg/box, the disease severity was 22.3.

Comparative Example 2

With the exception of not performing the application of the water-diluted flowable agent, the disease severity was calculated using the same method as that described for Example 1. The disease severity was 30.3.

<<Control of Rice Seedling Damping-Off (*Rhizopus* genus Fungus)>>

Example 2

A fungus culture of *Rhizopus chinensis* cultivated in a soil bran medium was mixed with a test soil to prepare a contaminated soil.

Small seedling boxes (8.5 cm×8.5 cm×3 cm) filled with this contaminated soil as the bed soil were irrigated by diluting the flowable agent obtained in Formulation Example 1 with water, and applying about 40 ml of the diluted agent uniformly to each seedling box. The active ingredient treatment amount was 2 mg/box.

Rice seeds (of the koshihikari variety) in the so-called hatomune state (in which a bud with a length of about 1 mm was protruding from each rice seed), prepared by subjecting the rice seeds to presoaking and forced germination treatments, were sowed across the entire surface of each seedling box, and an additional amount of the contaminated soil was then used to cover the seeds. The seedling boxes were then placed in a nursery cabinet at 34° C. for 3 days to allow the seeds to germinate. Subsequently, a low-temperature treatment at 4° C. was performed for 3 days. Following this low-temperature treatment, the seedlings were raised inside a glass greenhouse. Twenty two days after sowing, the number of healthy seedlings (A), the number of withered seedlings (B), the number of severely diseased seedlings (having a height less than ½ of that of the healthy seedlings) (C), and the number of lightly diseased seedlings (having a height of at least ½ but less than ¾ of that of the healthy seedlings) (D) within each seedling box were counted, and when the disease severity was calculated using the following formula, the result was 9.7.

Disease severity=($B$×3+$C$×2+$D$×1)/(number of seedlings×3)×100

Number of seedlings=$A$+$B$+$C$+$D$

Comparative Example 3

A chlorothalonil water-dispersible powder was diluted with water to obtain a chemical liquid having an active ingredient concentration of 0.08%.

With the exception of using this chemical liquid instead of the aforementioned water-diluted flowable agent, the disease severity was calculated using the same method as that described for Example 2. Although the active ingredient treatment amount was 16 mg/box, the disease severity was 11.4.

Comparative Example 4

With the exception of not performing the application of the water-diluted flowable agent, the disease severity was calculated using the same method as that described for Example 2. The disease severity was 20.2.

The above results indicate that the control method of the present invention exhibits a superior control effect against fungi of the genus *Fusarium* and the genus *Rhizopus* compared with conventional chemical reagents.

INDUSTRIAL APPLICABILITY

The present invention can provide a method for controlling phytopathogenic filamentous fungi other than oomycete microorganisms.

The invention claimed is:

1. A method for controlling *Rhizopus* genus Fungus and *Fusarium* genus Fungus in a rice in need thereof, consisting essentially of:

applying to the rice a formulation consisting essentially of an effective amount of at least one compound selected from the group consisting of a compound represented by formula (II) and salts thereof, and the amount of the compound represented by formula (II) incorporated within the formulation is within a range from 2 to 70% by mass:

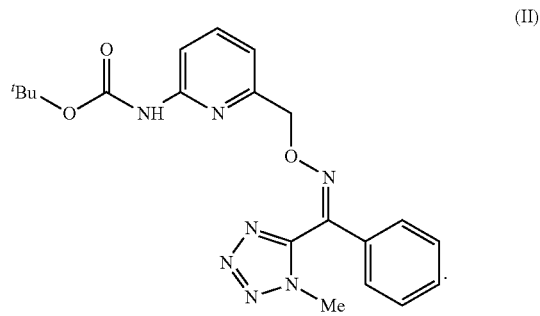 [SMILES: Cn1nnnc1/C(=N\OCc1cccc(NC(=O)OC(C)(C)C)n1)c1ccccc1]

(II)

2. The method according to claim 1, wherein the formulation is a flowable agent.

3. The method according to claim 1, wherein an active agent in the formulation consists of one or more compounds selected from the group consisting of the compound represented by formula (II) and salts thereof.

* * * * *